Dec. 17, 1974 W. A. WARRINER Plant Pat. 3,666
ROSE PLANT
Filed Oct. 24, 1973
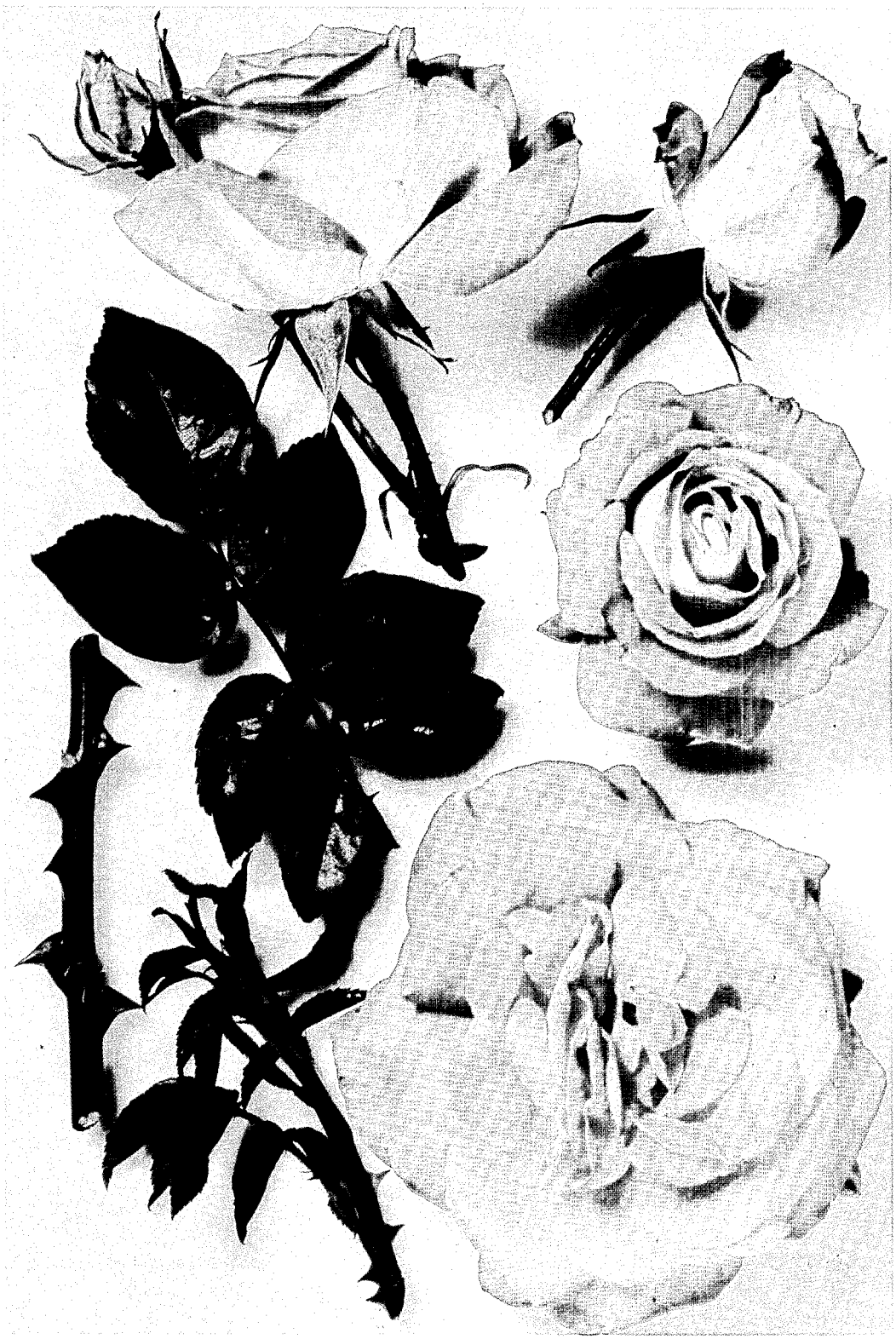

United States Patent Office

Plant Pat. 3,666
Patented Dec. 17, 1974

3,666
ROSE PLANT

William A. Warriner, Tustin, Calif., assignor to Jackson & Perkins Company, Medford, Oreg.

Filed Oct. 24, 1973, Ser. No. 409,270
Int. Cl. A01h 5/00
U.S. Cl. Plt.—12 1 Claim The present invention relates to a new and distinct cultivar or rose plant of the hybrid tea class which was originated by me by crossing the cultivar, Personality, U.S. Plant Pat. 2,097 with pollen from an unnamed cultivar.

The primary objective of this breeding was to produce a new rose cultivar of the hybrid tea class, with a bicolor or two-tone type of flower.

This objective was substantially achieved along with other desirable qualities as evidenced by the following unique combinations of characteristics which are outstanding in the new cultivar and which distinguish it from its parents as well as from all other cultivars of which I am aware:

1. A vigorous, upright, well branched habit of growth.
2. Large double flowers borne singly or in clusters.
3. Flower color of a clear Rose Madder on the upper side of the petals with a lighter tint of the same hue on the lower side.
4. Large, dark Parsley green, glossy foliage.
5. Little or no fragrance.

Asexual reproduction of this new cultivar by budding, as performed at Wasco, Calif., shows that the foregoing characteristics and distinctions come true to form and are established and transmitted through succeeding propagations.

The accompanying drawing shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with the *Royal Horticultural Society Color Chart,* except where ordinary dictionary significance of color is indicated.

Parentage: Seedling.
*Seed parent.*—Seedling of Personality.
*Pollen parent.*—Tropicana × Hallmark.
Classification:
*Botanic.*—Rosa hybrid.
*Commercial.*—Hybrid tea.

FLOWER

Observations were made at Irvine, Calif. in late June in the afternoon.

Blooming Habit: Recurrent—continuous.
Bud:
*Size.*—One to one and one-quarter inches when petals start to unfurl.
*Form.*—Pointed, ovoid.
*Color.*—When sepals first divide near Tyrian Rose (24 to 24/1) on lower side, irregularly overlaying a near white base; upper side much more intense, but of similar hue to Crimson (22) with a large yellow base (Primrose yellow 601/1). When half blown; upper side of petals near Rose Madder (23), lower side of petals near Rose Madder (23/3) or slightly lighter.
*Sepals.*—Color: Outer surface—Scheeles Green (860), heavily overlaid with Garnet Brown (00918/3). Inner surface—Similar to outer surface, covered with short white tomentum. Three appendaged sepals lightly appendaged. Two unappendaged sepals smooth edged.
*Receptacle.*—Color: Scheeles Green (860). Shape: Funnel. Size: Large. Surface: Smooth.
*Peduncle.*—Length: Medium. Surface: Prickly. Color: Bronzy. Strength: Stiff.
*Opening.*—Outer edges of petals roll back at tips, little or no "quilling" or pointed petals.

Bloom:
*Size.*—Large. Average size when fully expanded, four and one-half inches, five and one-half inches in early spring.
*Borne.*—Singly and several together.
*Stems.*—Long, strong.
*Form.*—When first open, high centered. Permanence—retains its form to the end.
*Petalage.*—Number of petals under normal conditions, 26–30.
*Color.*—Center of flowers: Upper side of petals—Rose Madder (23) with large basal area Primrose Yellow (601/1). Reverse side of petals—near Rose Madder (23/2). Outer petals: Upper side of petals—near Cherry (722). Reverse of petals—near Tyrian Rose (24 to 24/1), overlaying irregular areas near Rose Madder (23/3). Base of petals: Near white on lower side, Primrose Yellow above. General tonality from a distance—Rose Madder (23/2). No variegations.
*Discoloration.*—General tonality at end of first day Rose Madder (23). By third day near Rose Madder (23/2).
*Fragrance.*—None.
Petals:
*Texture.*—Thick.
*Surface.*—Inside—satiny. Reverse—satiny.
*Shape.*—Nearly deltoid with rounded points.
*Form.*—Tips slightly recurved.
*Arrangement.*—Imbricated.
*Petaloids in center.*—Few, large.
*Persistence.*—Drop off cleanly.
*Lastingness.*—On the plant—long. As cut flower—long.
Reproductive Parts:
*Stamens, Anthers.*—Medium. Color—yellow. Arrangement—regular around styles.
*Stamens, Filaments (threads).*—Both long and medium. Color—yellow.
*Pollen.*—Lemon yellow.
*Styles.*—Columnar, of uneven lengths.
*Stigmas.*—Color—yellow.
*Ovaries.*—All enclosed in calyx.
Fruit: Not observed.

PLANT

Form: Bush.
Growth: Very vigorous, upright and branching.
Foliage: Number of leaflets on normal mid-stem leaves, 5.
*Size.*—Large.
*Quantity.*—Normal.
*Color.*—New foliage: Garnet Brown (00918/3). Old foliage: Parsley Green (00962).
Leaflets:
*Shape.*—Oval pointed.
*Texture.*—Upper side—glossy. Under side—smooth. Ribs and veins—ordinary.
*Edge.*—Serrated.
*Serration.*—Single, small.
*Petiole.*—Rachis—Color—green. Underside—prickles.
*Stipules.*—Long.

*Disease Resistance.*—Moderately resistant to mildew, blackspot under normal growing conditions at Irvine, Calif.

Wood:

*New Wood.*—Color—reddish. Bark—smooth.

*Old Wood.*—Color—green with Garnet Brown overlay. Bark—smooth.

Prickles:

*Quantity.*—On main stalks from base—ordinary. On laterals—ordinary.

*Form.*—Broad based, hooked downwardly.

*Color.*—When young—brown.

*Position.*—Irregular.

Small prickles:

*Quantity.*—On main stalks—many. On laterals—many.

*Color.*—Brown.

I claim:

1. A new and distinct cultivar of rose plant of the hybrid tea class, substantially as herein shown and described, characterized particularly as to novelty by the unique combination of its vigorous, upright, well branched habit of growth; abundant quantities of blooms which are a clear Rose Madder on the upper sides of the petals while the under sides are a very light tint of Rose Madder; dark Parsley green, glossy foliage and lack of fragrance.

No references cited.

ROBERT E. BAGWILL, Examiner

UNITED STATES PATENT OFFICE
CERTIFICATE OF CORRECTION

Patent No. Plant 3666 Dated December 17, 1974

Inventor(s) William A. Warriner

It is certified that error appears in the above-identified patent and that said Letters Patent are hereby corrected as shown below:

Col. 1, line 2 "or" should be -- of --

Col. 2, line 29 "(23/2)" should be -- (23) --

Signed and sealed this 18th day of February 1975.

(SEAL)
Attest:

RUTH C. MASON
Attesting Officer

C. MARSHALL DANN
Commissioner of Patents
and Trademarks